United States Patent
Neya et al.

(10) Patent No.: US 9,403,691 B1
(45) Date of Patent: Aug. 2, 2016

(54) ZINC OXIDE POWDER, DISPERSION, PAINT, AND COSMETIC MATERIAL

(71) Applicant: Sumitomo Osaka Cement Co., Ltd., Tokyo (JP)

(72) Inventors: Tadashi Neya, Tokyo (JP); Tetsuro Itagaki, Tokyo (JP); Syunsuke Suma, Tokyo (JP)

(73) Assignee: Sumitomo Osaka Cement Co., Ltd., Tokyo (JP)

( * ) Notice: Subject to any disclaimer, the term of this patent is extended or adjusted under 35 U.S.C. 154(b) by 3 days.

(21) Appl. No.: 14/811,096

(22) Filed: Jul. 28, 2015

Related U.S. Application Data

(63) Continuation of application No. PCT/JP2015/061370, filed on Apr. 13, 2015.

(30) Foreign Application Priority Data

Jan. 30, 2015 (JP) ................................. 2015-017135

(51) Int. Cl.
| | |
|---|---|
| *A61Q 17/04* | (2006.01) |
| *C01G 9/02* | (2006.01) |
| *A61K 8/27* | (2006.01) |
| *C09D 7/12* | (2006.01) |

(52) U.S. Cl.
CPC ... *C01G 9/02* (2013.01); *A61K 8/27* (2013.01); *A61Q 17/04* (2013.01); *C09D 7/1216* (2013.01); *C09D 7/1225* (2013.01); *A61K 2800/591* (2013.01); *A61K 2800/651* (2013.01); *C01P 2004/62* (2013.01); *C01P 2006/12* (2013.01); *C01P 2006/40* (2013.01)

(58) Field of Classification Search
None
See application file for complete search history.

(56) References Cited

FOREIGN PATENT DOCUMENTS

| | | | |
|---|---|---|---|
| JP | 57205319 | A | 12/1982 |
| JP | 60255620 | A | 12/1985 |
| JP | 63288913 | A | 11/1988 |
| JP | 63288914 | A | 11/1988 |
| JP | 03199121 | A | 8/1991 |
| JP | 07232919 | A | 9/1995 |
| JP | 2002201024 | A | 7/2002 |
| JP | 2002201382 | A | 7/2002 |
| JP | 2005534607 | A | 11/2005 |
| JP | 2008230915 | A | 10/2008 |
| JP | 2010508230 | A | 3/2010 |
| WO | 0046152 | A1 | 8/2000 |
| WO | 2004058645 | A1 | 7/2004 |
| WO | 2012147888 | A1 | 11/2012 |

OTHER PUBLICATIONS

Atushi Kishimoto, Chou Biryuushi Sanka Aen ni tsuite, Tosou to Toryou, 1997, No. 570, p. 27-33.
Atushi Kishimoto, Chuo Biryuushi Sanka Aen ni tsuite, Tosou to Toryou, 1997, No. 570, p. 27-33.
Office Action issued in Japanese Patent Application No. 2015-017135, mailed Jun. 16, 2015, 13 pages.
International Search Report issued in International Patent Application No. PCT/JP2015/061370, mailed Jul. 7, 2015, 4 pages.

*Primary Examiner* — Abigail Fisher
*Assistant Examiner* — Frank Choi
(74) *Attorney, Agent, or Firm* — Wood, Herron & Evans, LLP

(57) ABSTRACT

Zinc oxide powder of the present invention has a specific surface area which is in a range of 1.5 m²/g to 65 m²/g, a conductivity which is 150 μS/cm or less and a bulk specific volume which is in a range of 0.5 mL/g to 10 mL/g.

20 Claims, No Drawings

ZINC OXIDE POWDER, DISPERSION, PAINT, AND COSMETIC MATERIAL

TECHNICAL FIELD

The present invention relates to zinc oxide powder, a dispersion, paint and a cosmetic material.

The present application claims priority on the basis of Japanese Patent Application No. 2015-017135 filed on Jan. 30, 2015 and the content thereof is incorporated herein by reference.

BACKGROUND ART

Zinc oxide has an ultraviolet-shielding function, a gas transmission-suppressing function and the like, and is also highly transparent. Therefore, zinc oxide is used for applications requiring transparency such as an ultraviolet-shielding film, ultraviolet-shielding glass, a cosmetic material and a gas barrier film.

As one of methods for obtaining transparency, the primary particle diameter of zinc oxide particles is decreased. As a method for manufacturing zinc oxide fine particles, a variety of methods such as a thermal decomposition method and a gas phase method are being studied (for example, Patent Documents 1 to 7).

CONVENTIONAL ART DOCUMENTS

Patent Documents

Patent Document 1: Japanese Unexamined Patent Application, First Publication No. S 57-205319
Patent Document 2: Japanese Unexamined Patent Application, First Publication No. S 60-255620
Patent Document 3: Japanese Unexamined Patent Application, First Publication No. S 63-288913
Patent Document 4: Japanese Unexamined Patent Application, First Publication No. S 63-288914
Patent Document 5: Japanese Unexamined Patent Application, First Publication No. H 3-199121
Patent Document 6: Japanese Unexamined Patent Application, First Publication No. H 7-232919
Patent Document 7: Japanese Unexamined Patent Application, First Publication No. 2002-201382

DISCLOSURE OF THE INVENTION

Problem to be Solved by the Invention

Zinc oxide fine particles are highly transparent, but have high surface energy since they are fine particles. Therefore, it is difficult to directly blend this powder into a final product such as a cosmetic material. In addition, while having small primary particle diameters, zinc oxide fine particles agglomerate together depending on the blending method and it is difficult to maintain high transparency. Therefore, in order to prevent the particles from agglomerating together, generally, a method is used in which a dispersion is produced by dispersing zinc oxide powder in a dispersion medium and the dispersion is mixed with other components.

The dispersion including zinc oxide powder (hereinafter, may be referred to as "zinc oxide dispersion") preferably has a great content of the zinc oxide powder, that is, has a high solid content concentration. The reasons thereof are as follows. For example, in a case in which improvement of the ultraviolet-shielding function of zinc oxide is requested, it is necessary to increase the content of zinc oxide powder in a zinc oxide dispersion. When the content of the zinc oxide powder is small and therefore the solid content concentration is low, the amount of a dispersion medium blended in becomes large as compared with a case in which a solid content concentration is high. Therefore, the content of other components decreases, the degree of freedom in formulation becomes low, and the number of functions that can be imparted is also small.

However, as the content of the zinc oxide powder in the zinc oxide dispersion increases, the fluidity of the zinc oxide dispersion becomes low and it becomes difficult to sufficiently stir the zinc oxide dispersion using a mixer, a mill or the like. Therefore, there has been a problem in that a uniform zinc oxide dispersion having a high solid content concentration cannot be obtained.

The present invention has been made in consideration of the above-described circumstances, and an object of the present invention is to provide zinc oxide powder that can be dispersed in a dispersion medium in a state in which a solid content concentration thereof is high, and a dispersion, paint and a cosmetic material which include the zinc oxide powder.

Means for Solving the Problems

Zinc oxide powder of the present invention is characterized in which a specific surface area of the powder is in a range of 1.5 m$^2$/g to 65 m$^2$/g, a conductivity of the powder is 150 µS/cm or less, and a bulk specific volume of the powder is in a range of 0.5 mL/g to 10 mL/g.

A dispersion of the present invention includes: the zinc oxide powder of the present invention and a dispersion medium, in which the content of the zinc oxide powder is in a range of 50% by mass to 90% by mass.

Paint of the present invention includes: the zinc oxide powder of the present invention, a resin, and a dispersion medium, in which the content of the zinc oxide powder is in a range of 10% by mass to 40% by mass.

A cosmetic material of the present invention includes: at least one selected from a group consisting of the zinc oxide powder of the present invention and the dispersion of the present invention.

Effects of Invention

According to the zinc oxide powder of the present invention, since the specific surface area thereof is in a range of 1.5 m$^2$/g to 65 m$^2$/g, the conductivity thereof is 150 µS/cm or less, and the bulk specific volume thereof is in a range of 0.5 mL/g to 10 mL/g, it is possible to provide a dispersion including zinc oxide powder having a high solid content uniformly. The inventors of the present invention found that, when the above-described three characteristics are combined together, it is possible to obtain unexpected effects that have not been known thus far.

According to the dispersion of the present invention, since the zinc oxide powder of the present invention and a dispersion medium are included and the content of the zinc oxide powder is in a range of 50% by mass to 90% by mass, in a case in which the dispersion is mixed with other components, it is possible to decrease the amount of the dispersion medium, that is added to the dispersion, to obtain the desired effects of zinc oxide.

According to the paint of the present invention, since the zinc oxide powder of the present invention, a resin and a dispersion medium are included in the paint and the content of the zinc oxide powder is in a range of 10% by mass to 40% by mass, it is possible to obtain paint which includes a high concentration of a solid content (zinc oxide powder) and in which the zinc oxide powder is uniformly dispersed.

According to the cosmetic material of the present invention, since the cosmetic includes at least one selected from a group consisting of the zinc oxide powder of the present invention and the dispersion of the present invention, it is possible to improve the degree of freedom in formulation through which other components are blended in.

BEST MODE FOR CARRYING OUT THE INVENTION

Preferred embodiments of the zinc oxide powder, the dispersion, the paint and the cosmetic material of the present invention will be described below.

Meanwhile, the present embodiments are simply specific descriptions for the better understanding of the gist of the present invention, and do not limit the present invention unless particularly specified.

[Zinc Oxide Powder]

In zinc oxide powder of the present embodiment, the specific surface area thereof is in a range of 1.5 $m^2/g$ to 65 $m^2/g$, the conductivity thereof is 150 μS/cm or less, and the bulk specific volume thereof is in a range of 0.5 mL/g to 10 mL/g.

The zinc oxide powder of the present invention may be manufactured using the methods described in Patent Documents 1 to 7; however, in order to obtain the properties of the invention of the present application, it is necessary to carry out steps such as washing, the selection of materials and the selection of manufacturing conditions as necessary.

For the zinc oxide powder of the present embodiment, the specific surface area refers to a value measured using an automatic surface area measurement instrument (product name: Macsorb HM Model-1201, manufactured by Mountech Co., Ltd.) according to the BET method.

For the zinc oxide powder of the present embodiment, the conductivity refers to a value measured using the following method.

Zinc oxide powder (10 g) and pure water (75 g) are mixed together, and this liquid mixture is boiled on a hot plate for 10 minutes. Next, the liquid mixture is cooled in the air to room temperature and then pure water is added to the liquid mixture so that the total amount of the zinc oxide powder and the pure water reaches 85 g. Next, the liquid mixture is separated into solid and liquid through centrifugal separation, and the conductivity of the supernatant liquid is measured using a conductivity meter (product name: ES-12, manufactured by Horiba, Ltd.).

For the zinc oxide powder of the present embodiment, the bulk specific volume refers to a value measured according to JIS K5101-12-1 (Test methods for pigments-Part 12: Apparent density or apparent specific volume-Section 1: Loose packing method).

The conductivity of the zinc oxide powder of the present embodiment is 150 μS/cm or less, preferably 100 μS/cm or less, more preferably 50 μS/cm or less, still more preferably 30 μS/cm or less and most preferably 10 μS/cm or less. In addition, the lower limit value of the conductivity of the zinc oxide powder of the present embodiment is 0 μS/cm.

When the conductivity of the zinc oxide powder is set to 150 μS/cm or less, it is possible to uniformly disperse the zinc oxide powder at a high concentration in a dispersion medium.

When the conductivity exceeds 150 μS/cm, since the zinc oxide powder is included at a high concentration, the influence of an ion component derived from the zinc oxide powder on the charge balance of the dispersion becomes large and the dispersion stability degrades, which is not preferable. In addition, even in a case in which a dispersant is used, since the zinc oxide powder is included at a high concentration, the ion component derived from the zinc oxide powder is adsorbed to the dispersant, an effect that hinders the dispersion effect becomes large, and the dispersion stability degrades, which is not preferable.

As a method for adjusting the conductivity of the zinc oxide powder to the above-described range, for example, there is a method in which the content of impurities in the zinc oxide powder is decreased. Therefore, in a case in which zinc oxide powder is produced, zinc oxide powder having a low conductivity can be obtained by using a highly-pure raw material, appropriately adjusting the thermal decomposition temperature in the production step, preventing impurities from being mixed in the production step, providing an appropriate washing step in the process of the production step or the like.

In addition, in the zinc oxide powder of the present embodiment, the content of substances that are soluble in water (hereinafter, referred to as "water-soluble substances") is preferably small. Specifically, the content of the water-soluble substances in the zinc oxide powder is preferably 0.08% by mass or less, and more preferably 0.05% by mass or less.

When the content of the water-soluble substances in the zinc oxide powder is set to the above-described range, that is, is set to be as low as possible, the water-soluble substances derived from the zinc oxide powder in the dispersion do not easily hinder the stability of the dispersion. Therefore, even when zinc oxide is dispersed at a high concentration, it is possible to maintain the stability of the dispersion.

The content of the water-soluble substances in the zinc oxide powder of the present embodiment refers to a value measured using the following method. Meanwhile, this measurement method is based on "67. Test methods for water-soluble substances" described in Japanese Standards of Quasi-drug Ingredients 2006 (JSQI).

Zinc oxide powder (5 g) is weighed, pure water (70 mL) is added to the zinc oxide powder, and the liquid mixture of the zinc oxide powder and pure water is boiled for five minutes. Next, the liquid mixture is cooled, then, pure water is further added to the liquid mixture so that the total amount reaches 100 mL, furthermore, the pure water and the liquid mixture are mixed together, and then the mixture is filtered. Next, the first 10 mL of the filtrate is removed and the subsequently-obtained 40 mL of the filtrate is sampled. The sampled filtrate is evaporated and solidified on a water bath, and subsequently is dried at 105° C. for one hour, and the mass of the dried residue is measured. The percentage of a value which is obtained by dividing the mass of the dried residue by the initially-weighed mass of the zinc oxide powder is used as the content of the water-soluble substances in the zinc oxide powder.

As preferred embodiments of the zinc oxide powder of the present embodiment, there are a first embodiment and a second embodiment described below.

First Embodiment

The specific surface area of the zinc oxide powder of the first embodiment is in a range of 8 $m^2/g$ to 65 $m^2/g$, preferably in a range of 15 $m^2/g$ to 60 $m^2/g$, more preferably in a range of 20 $m^2/g$ to 50 $m^2/g$, and still more preferably in a range of 25 $m^2/g$ to 45 $m^2/g$.

When the specific surface area of the zinc oxide powder is adjusted to the above-described range, it is possible to disperse the zinc oxide powder at a high concentration in a dispersion medium. Additionally, it is possible to make the dispersion, paint, the cosmetic material and the like, which include the zinc oxide powder more transparent.

When the specific surface area is less than 8 m²/g, there is a tendency that the transparency of the dispersion degrades in a case in which the zinc oxide powder is included at a high concentration, and such tendency is not preferable. On the other hand, when the specific surface area exceeds 65 m²/g, there is a tendency that the viscosity of the dispersion easily increases in a case in which the zinc oxide powder is included at a high concentration, and it becomes difficult to obtain a uniform dispersion having high fluidity. Such tendency is not preferable.

The method for adjusting the specific surface area of the zinc oxide powder to the above-described range is not particularly limited. Examples thereof include a method in which the average primary particle diameter (average particle diameter) converted from the BET specific surface area is adjusted to 15 nm to 135 nm. Generally, the specific surface area decreases as the primary particle diameter increases and the specific surface area increases as the primary particle diameter decreases.

In addition, it is possible to adjust the specific surface area of the zinc oxide powder by adjusting the particle shapes or providing fine pores among the particles.

The bulk specific volume of the zinc oxide powder of the first embodiment is in a range of 1 mL/g to 10 mL/g, preferably in a range of 1.5 mL/g to 9.5 mL/g, more preferably in a range of 3.0 mL/g to 8.0 mL/g, and still more preferably in a range of 4.0 mL/g to 7.0 mL/g.

When the bulk specific volume of the zinc oxide powder is adjusted to the above-described range, it is possible to uniformly disperse the zinc oxide powder at a high concentration in a dispersion medium.

When the bulk specific volume is less than 1 mL/g, there is a tendency that the transparency of the dispersion degrades in a case in which the zinc oxide powder is included at a high concentration, and such a tendency is not preferable. On the other hand, when the bulk specific volume exceeds 10 mL/g, there is a tendency that the viscosity of the dispersion easily increases in a case in which the zinc oxide powder is included at a high concentration, and it becomes difficult to obtain a uniform dispersion having high fluidity. Such a tendency is not preferable.

The method for controlling the bulk specific volume of the zinc oxide powder to the above-described range is not particularly limited.

For example, in a case in which the zinc oxide powder is produced using the thermal decomposition method as described in Patent Document 2, it is possible to control the bulk specific volume of the zinc oxide powder to the above-described range by adjusting the bulk specific volume of zinc oxalate, zinc hydroxide, zinc carbonate, basic zinc carbonate and the like, which can be served as a raw material, adjusting the thermal decomposition temperature or the like.

For example, in a case in which the zinc oxide powder is produced using the gas phase method as described in Patent Document 4, it is possible to control the bulk specific volume of the zinc oxide powder to the above-described range by appropriately adjusting the temperature in the production process.

The average particle diameter of the zinc oxide powder of the first embodiment can be arbitrarily selected. For example, generally, it is possible to use the zinc oxide powder having an average particle diameter preferably in a range of 15 nm to 75 nm, more preferably in a range of 20 nm to 55 nm, and still more preferably in a range of 25 nm to 45 nm. For the average particle diameter, the BET specific surface area value can be computed using Equation (1). This conversion method also shall apply to the second embodiment.

$$\text{Average particle diameter}=6000/(BET\text{ specific surface area}\times\rho) \tag{1}$$

(In the equation, $\rho$ represents the density of zinc oxide particles and, in the present specification, $\rho$ is set to 5.606 g/cm³ for conversion.)

The method for manufacturing the zinc oxide powder of the first embodiment is not particularly limited. The manufacturing method preferably includes the above-described method for adjusting the specific surface area of the zinc oxide powder, the above-described method for adjusting the conductivity of the zinc oxide powder, the above-described method for adjusting the bulk specific volume of the zinc oxide powder and the like, and these adjustment methods are appropriately carried out depending on the application of the zinc oxide powder.

As an example of a method of the method for manufacturing the zinc oxide powder of the first embodiment, there is a method in which zinc carbonate having a bulk specific volume in a range of 1.0 mL/g to 10.0 mL/g is thermally decomposed and sintered (grain growth) at a temperature in a range of 300° C. to 700° C. and preferably in a range of 400° C. to 600° C.

Second Embodiment

The specific surface area of the zinc oxide powder of the present embodiment is in a range of 1.5 m²/g to less than 8.0 m²/g, preferably in a range of 2.0 m²/g to 7.5 m²/g, and more preferably in a range of 3.0 m²/g to 7.0 m²/g.

When the specific surface area of the zinc oxide powder is adjusted to the above-described range, it is possible to disperse the zinc oxide powder at a high concentration in a dispersion medium. Additionally, it is possible to maintain the transparency of a dispersion, paint, a cosmetic material and the like which include the zinc oxide powder.

Zinc oxide powder having a specific surface area in the above-described range is preferred since the zinc oxide powder can be used with natural oil.

Here, the natural oil is not particularly limited as long as the natural oil is a nature-derived oil component and can be used as a cosmetic material. The natural oil may be derived from plants or animals. Examples of the natural oil include oleic acid, jojoba oil, olive oil, coconut oil, grape seed oil, castor oil, rice bran oil, horse oil, mink oil, squalane and the like.

In addition, zinc oxide powder having a specific surface area in the above-described range has a critical wavelength of 370 nm or more, and a cosmetic material including the zinc oxide powder is capable of shielding ultraviolet rays in a wide range of long-wavelength ultraviolet rays (UVA) and short-wavelength ultraviolet rays (UVB), and such a shielding is preferable.

When the specific surface area is less than 1.5 m²/g, there is a tendency that the transparency of the dispersion degrades in a case in which the zinc oxide powder is included at a high concentration, and such a tendency is not preferable. On the other hand, when the specific surface area is 8.0 m²/g or more, there is a tendency that the viscosity of the dispersion easily increases in a case in which the zinc oxide powder is included at a high concentration, and it becomes difficult to obtain a uniform dispersion having high fluidity. Such a tendency is not preferable.

The method for adjusting the specific surface area of the zinc oxide powder to the above-described range is not particularly limited. Examples thereof include a method in which the average primary particle diameter converted from the BET specific surface area is preferably adjusted to more than 135 nm to 715 nm, more preferably adjusted to 140 nm to 535 nm, and still more preferably adjusted to 150 nm to 360 nm.

The bulk specific volume of the zinc oxide powder of the second embodiment is in a range of 0.5 mL/g to 6 mL/g, preferably in a range of 1 mL/g to 5 mL/g, and more preferably in a range of 2 mL/g to 4 mL/g.

When the bulk specific volume of the zinc oxide powder is set to the above-described range, it is possible to uniformly disperse the zinc oxide powder at a high concentration in a dispersion medium.

When the bulk specific volume is less than 0.5 mL/g, there is a tendency that the transparency of the dispersion degrades in a case in which the zinc oxide powder is included at a high concentration, and such a tendency is not preferable. On the other hand, when the bulk specific volume exceeds 6 mL/g, there is a tendency that the viscosity of the dispersion easily increases in a case in which the zinc oxide powder is included at a high concentration, and it becomes difficult to obtain a uniform dispersion having high fluidity. Such a tendency is not preferable.

The method for controlling the bulk specific volume of the second embodiment to the above-described range is not particularly limited. For example, the bulk specific volume can be controlled in the same manner as in the first embodiment.

The maximum value of the primary particle diameter of the zinc oxide powder of the second embodiment is preferably 900 nm or less, more preferably 800 nm or less, still more preferably 600 nm or less, and most preferably 400 nm or less.

In a case in which zinc oxide having a primary particle diameter of more than 900 nm is included, the appearance becomes white when a cosmetic material produced using the zinc oxide powder is applied to the skin, and such appearance is not preferable.

In the second embodiment, the primary particle diameter means a diameter which is obtained by selecting 150 primary particles of zinc oxide using a scanning electron microscope (SEM) and determining the longest diameter from multiple diameters passing through the center point of the particles.

In the second embodiment, the maximum value of the primary particle diameter refers to the largest value selecting from the primary particle diameters measured from the 150 particles using the above-described method.

The method for manufacturing the zinc oxide powder of the second embodiment is not particularly limited. The manufacturing method preferably includes the above-described method for adjusting the specific surface area of the zinc oxide powder, the above-described method for adjusting the conductivity of the zinc oxide powder, the above-described method for adjusting the bulk specific volume of the zinc oxide powder and the like, and these adjustment methods are appropriately carried out depending on the application of the zinc oxide powder.

As an example of a method of the method for manufacturing the zinc oxide powder of the second embodiment, there is a method in which zinc carbonate having a bulk specific volume in a range of 0.5 mL/g to 6 mL/g is thermally decomposed and sintered (grain growth) at a temperature in a range of 300° C. to 1000° C. and preferably in a range of 400° C. to 800° C.

[Surface-Treated Zinc Oxide Powder]

For the zinc oxide powder of the present embodiment, at least a part of the surface thereof may be treated with at least one of an inorganic component and an organic component. The zinc oxide powder that is surface-treated with at least one of an inorganic component and an organic component as described above is referred to as the surface-treated zinc oxide powder.

The inorganic component and the organic component are appropriately selected depending on the applications of the zinc oxide powder.

In a case in which the surface-treated zinc oxide powder of the present embodiment is used for a cosmetic material, there is no particular limitation regarding the inorganic component and the organic component as long as the components are surface treatment agents that are generally used for cosmetic materials.

The inorganic component is, for example, at least one selected from silica, alumina and the like.

The organic component is, for example, at least one selected from a silicone compound, an organopolysiloxane, a fatty acid, a fatty acid soap, a fatty acid ester and an organic titanate compound.

In addition, a surfactant may be used as the inorganic component or the organic component.

In a case in which the zinc oxide powder is surface-treated with at least one of the inorganic component and the organic component, it is possible to suppress the surface activity of zinc oxide or improve the dispersibility of zinc oxide in a dispersion medium.

Examples of the silicone compound used for the surface treatment include: silicone oil such as methyl hydrogen polysiloxane, dimethyl polysiloxane and methyl phenyl polysiloxane; alkylsilane such as methyl trimethoxysilane, ethyl trimethoxysilane, hexyl trimethoxysilane and octyl trimethoxysilane; fluoroalkyl silane such as trifluoro methyl ethyl trimethoxysilane and heptadecafluorodecyl trimethoxysilane; methicone, hydrogen dimethicone, triethoxysilylethyl polydimethylsiloxyethyl dimethicone, triethoxysilylethyl polydimethylsiloxyethylhexyl dimethicone, (acrylate/tridecyl acrylate/triethoxysilylpropyl methacrylate/dimethicone methacrylate) copolymers, triethoxycaprylylsilane and the like. These silicone compounds may be used singly, or a combination of two or more silicone compounds may be used. In addition, as the silicone compound, a copolymer of these silicone compounds may be used.

Examples of the fatty acid include palmitic acid, isostearic acid, stearic acid, lauric acid, myristic acid, behenic acid, oleic acid, rosin acid, 12-hydroxystearic acid and the like.

Examples of the fatty acid soap include aluminum stearate, calcium stearate, aluminum 12-hydroxystearate and the like.

Examples of the fatty acid ester include dextrin fatty acid esters, cholesterol fatty acid esters, sucrose fatty acid esters, starch fatty acid esters and the like.

Examples of the organic titanate compound include isopropyl triisostearoyl titanate, isopropyl dimethacryl isostearoyl titanate, isopropyl tri(dodecyl) benzene sulfonyl titanate, neopentyl (diallyl)oxy tri(dioctyl) phosphate titanate, neopentyl (diallyl)oxy trineodododecanoyl titanate and the like.

In a case in which the surface-treated zinc oxide powder of the present embodiment is used for an industrial application such as an ultraviolet-shielding film or a gas barrier film, in addition to the inorganic component or the organic component used for cosmetic materials, it is also possible to appropriately select and use a dispersant such as an anionic dispersant, a cationic dispersant, a nonionic dispersant, a silane coupling agent, or a wetting dispersant, that is, it is possible to use an ordinary dispersant which is used to disperse particles.

In a case in which the above-described surface treatment is carried out, it is possible to suppress the surface activity of zinc oxide or improve the dispersibility of zinc oxide in a dispersion medium.

There is no particular limitation regarding the method for manufacturing the surface-treated zinc oxide powder of the present embodiment, and a well-known method may be appropriately carried out depending on the components used in the surface treatment.

[Dispersion]

A dispersion of the present embodiment includes the zinc oxide powder of the present embodiment and a dispersion medium, and the content of the zinc oxide powder is in a range of 50% by mass to 90% by mass.

Meanwhile, the dispersion of the present embodiment may be a paste-form dispersion having a high viscosity. In addition, the dispersion of the present embodiment includes the zinc oxide powder of the first embodiment or the zinc oxide powder of the second embodiment as the zinc oxide powder. Furthermore, the dispersion of the present embodiment includes at least one of zinc oxide powder having untreated surfaces and zinc oxide powder having surfaces that are at least partially treated with at least one of the inorganic component and the organic component (surface-treated zinc oxide powder) as the zinc oxide powder.

The content of the zinc oxide powder in the dispersion of the present embodiment is in a range of 50% by mass to 90% by mass, preferably in a range of 60% by mass to 80% by mass, more preferably in a range of 64% by mass to 75% by mass, and still more preferably in a range of 64% by mass to 70% by mass.

When the content of the zinc oxide powder in the dispersion is within the above-described range, it is possible to obtain a dispersion which includes a high concentration of a solid content (zinc oxide powder) and in which the zinc oxide powder is uniformly dispersed.

Meanwhile, "the zinc oxide powder being uniformly dispersed" means that, when the dispersion is visually observed, the zinc oxide powder is not separated and is in an evenly-mixed state.

The viscosity of the dispersion of the present embodiment is preferably in a range of 5 Pa·s to 300 Pa·s, more preferably in a range of 8 Pa·s to 100 Pa·s, still more preferably in a range of 10 Pa·s to 80 Pa·s and most preferably in a range of 15 Pa·s to 60 Pa·s.

When the viscosity of the dispersion is within the above-described range, it is possible to obtain a dispersion that can be easily handled even when the solid content (zinc oxide powder) is included at a high concentration.

Meanwhile, the preferred range of the viscosity of the dispersion of the present embodiment similarly applies to both a dispersion including zinc oxide powder having untreated surfaces and a dispersion including surface-treated zinc oxide powder as the zinc oxide powder.

The dispersion medium is appropriately selected depending on the application of the dispersion. Examples of preferred dispersion media will be described below, but the dispersion medium in the present embodiment is not limited thereto.

As the dispersion medium, for example, water, alcohols such as methanol, ethanol, 1-propanol, 2-propanol, 1-butanol, 2-butanol, octanol, and glycerin; esters such as ethyl acetate, butyl acetate, ethyl lactate, propylene glycol monomethyl ether acetate, propylene glycol monoethyl ether acetate and γ-butyrolactone; and ethers such as diethyl ethers, ethylene glycol monomethyl ethers (methyl cellosolves), ethylene glycol monoethyl ethers (ethyl cellosolves), ethylene glycol monobutyl ethers (butyl cellosolves), diethylene glycol monomethyl ethers, and diethylene glycol monoethyl ethers can be preferable used.

These dispersion media may be used singly, or a mixture of two or more dispersion media may be used.

In addition, as the dispersion medium, ketones such as acetone, methyl ethyl ketone, methyl isobutyl ketone, acetyl acetone and cyclohexanone; aromatic hydrocarbons such as benzene, toluene, xylene and ethyl benzene; cyclic hydrocarbon such as cyclohexane; amides such as dimethylformamide, N,N-dimethylacetoacetamide, and N-methylpyrrolidone; and chain-like polysiloxanes such as dimethyl polysiloxane, methyl phenyl polysiloxane and diphenyl polysiloxane can also be preferably used.

These dispersion media may be used singly, or a mixture of two or more dispersion media may be used.

In addition, as the dispersion medium, cyclic polysiloxanes such as octamethyl cyclotetrasiloxane, decamethyl cyclopentasiloxane and dodecamethyl cyclohexasiloxane; and denatured polysiloxanes such as amino-denatured polysiloxane, polyether-denatured polysilocane, alkyl-denatured polysiloxane and fluorine-denatured polysiloxane can also be preferably used.

These dispersion media may be used singly, or a mixture of two or more dispersion media may be used.

In addition, as the dispersion medium that is different from the above-described dispersion media, hydrophobic dispersion media may also be used such as hydrocarbon oils such as liquid paraffin, squalane, isoparaffin, branched chain-like light paraffin, petrolatum, and ceresin, ester oils such as isopropyl myristate, cetyl isooctanoate and glyceryl trioctanoate, silicone oils such as decamethyl cyclopentasiloxane, dimethyl polysiloxane, and methyl phenyl polysiloxane, higher fatty acids such as lauric acid, myristic acid, palmitic acid and stearic acid, and higher alcohols such as lauryl alcohol, cetyl alcohol, stearyl alcohol, hexyl dodecanol and isostearyl alcohol.

These dispersion media may be used singly, or a mixture of two or more dispersion media may be used.

The above-described examples of a variety of dispersion media may be used singly, or a mixture of two or more dispersion media may be used as necessary.

The dispersion of the present embodiment may include ordinarily-used additives as long as the characteristics thereof are not impaired. Examples of the additives include dispersants, stabilizers, water-soluble binders, viscosity improvers, oil-soluble preservatives, ultraviolent absorbers, oil-soluble chemicals, oil-soluble pigments, oil-soluble proteins, plant oils, animal oils and the like.

Among the dispersions of the embodiment, the critical wavelength of the dispersion which includes the above-described zinc oxide powder of the second embodiment out of the dispersions of the present embodiment is preferably 370 nm or more. When the critical wavelength of the dispersion is 370 nm or more, the critical wavelength of a cosmetic material including the dispersion reaches 370 nm or more, and it is possible to shield ultraviolet rays in a wide range of long-wavelength ultraviolet rays (UVA) and short-wavelength ultraviolet rays (UVB).

Meanwhile, the above preferred range of the critical wavelength of the dispersion of the present embodiment similarly applies to both a dispersion including zinc oxide powder having untreated surfaces and a dispersion including surface-treated zinc oxide powder as the zinc oxide powder.

The method for manufacturing the dispersion of the present embodiment is not particularly limited. Examples thereof include a method in which the zinc oxide powder of the present embodiment and a dispersion medium are mechanically dispersed using a well-known dispersion apparatus.

The dispersion apparatus can be selected in accordance with the necessity, and examples thereof include a stirrer, a planetary mixer, a homo mixer, an ultrasonic homogenizer, a sand mill, a ball mill, a roll mill and the like.

The dispersion of the present embodiment can be used for paint which has an ultraviolet-shielding function, a gas transmission-suppressing function or the like in addition to cosmetic materials.

[Paint]

Paint of the present embodiment includes the zinc oxide powder of the present embodiment, a resin, and a dispersion medium, and the content of the zinc oxide powder is in a range of 10% by mass to 40% by mass.

The dispersion of the present embodiment includes the zinc oxide powder of the first embodiment or the zinc oxide powder of the second embodiment as the zinc oxide powder.

The content of the zinc oxide powder in the paint of the present embodiment is in a range of 10% by mass to 40% by mass, preferably in a range of 15% by mass to 35% by mass and more preferably in a range of 20% by mass to 30% by mass.

When the content of the zinc oxide powder in the paint is within the above-described range, it is possible to obtain paint which includes a high concentration of the solid content (zinc oxide powder) and in which the zinc oxide powder is uniformly dispersed.

The dispersion medium is not particularly limited as long as the dispersion medium is ordinarily used for industrial applications. Examples thereof include water, alcohols such as methanol, ethanol and propanol and organic solvents such as methyl acetate, ethyl acetate, toluene, methyl ethyl ketone and methyl isobutyl ketone.

These dispersion media may be used singly, or a mixture of two or more dispersion media may be used.

The content of the dispersion medium in the paint of the present embodiment is not particularly limited, and is appropriately adjusted in accordance with the intended characteristics of the paint.

The resin is not particularly limited as long as the resin is generally used for industrial applications. Examples thereof include an acrylic resin, an epoxy resin, a urethane resin, a polyester resin, a silicone resin and the like.

These resins may be used singly, or a mixture of two or more resins may be used.

The content of the resin in the paint of the present embodiment is not particularly limited, and is appropriately adjusted in accordance with the intended characteristics of the paint.

The paint of the present embodiment may include ordinarily-used additives as long as the characteristics thereof are not impaired. Examples of the additives include polymerization initiators, dispersants, preservatives and the like.

There is no particular limitation regarding the method for manufacturing the paint of the present embodiment. Examples thereof include a method in which the zinc oxide powder of the present embodiment, the resin, and the dispersion medium are mechanically mixed together using a well-known dispersion apparatus.

In addition, there is another method in which the above-described dispersion and the resin are mechanically mixed together using a well-known mixing apparatus.

Examples of the mixing apparatus include a stirrer, a planetary mixer, a homo mixer, an ultrasonic homogenizer and the like.

When the paint of the present embodiment is applied to a base material which is selected in accordance with the necessity, for example, a plastic base material such as a polyester film or the like, it is possible to form a coated film using an ordinary application method such as a roll coating method, a flow coating method, a spray coating method, a screen printing method, a brush coating method, or an immersion method. The paint can be used as an ultraviolet-shielding film or a gas barrier film.

[Cosmetic Material]

A cosmetic material of an embodiment of the present embodiment includes at least one selected from the group consisting of the zinc oxide powder of the present embodiment and the dispersion of the present embodiment.

A cosmetic material of another embodiment includes a base and at least one selected from the group consisting of the zinc oxide powder of the present embodiment and the dispersion of the present embodiment which are dispersed in the base.

The cosmetic material of the present embodiment includes the zinc oxide powder of the first embodiment or the zinc oxide powder of the second embodiment as the zinc oxide powder.

The cosmetic material of the present embodiment can be obtained by, for example, blending the dispersion of the present embodiment into a base such as an emulsion, cream, foundation, a lip stick, a blusher or an eye shadow as done in the related art.

In addition, it is also possible to blend the zinc oxide powder of the present embodiment into an oil phase or a water phase so as to produce an O/W-type or W/O-type emulsion and then blend the emulsion with the base.

Hereinafter, a sunscreen cosmetic material will be specifically described.

The content rate of the zinc oxide powder in the sunscreen cosmetic material is preferably in a range of 1% by mass to 30% by mass, more preferably in a range of 3% by mass to 20% by mass, and still more preferably in a range of 5% by mass to 15% by mass in order to effectively shield ultraviolet rays, particularly, long-wavelength ultraviolet rays (UVA).

The sunscreen cosmetic material may include a hydrophobic dispersion medium, inorganic fine particles or an inorganic pigment other than the zinc oxide powder, a hydrophilic dispersion medium, fat and oil, a surfactant, a moisturizing agent, a viscosity improver, a pH adjuster, a nutritional supplement, an antioxidant, a perfume and the like as necessary.

Examples of the hydrophobic dispersion medium include hydrocarbon oils such as liquid paraffin, squalane, isoparaffin, branched chain-like light paraffin, petrolatum, and ceresin, ester oils such as isopropyl myristate, cetyl isooctanoate and glyceryl trioctanoate, silicone oils such as decamethyl cyclopentasiloxane, dimethyl polysiloxane, and methyl phenyl polysiloxane, higher fatty acids such as lauric acid, myristic acid, palmitic acid and stearic acid, and higher alcohols such as lauryl alcohol, cetyl alcohol, stearyl alcohol, hexyl dodecanol, and isostearyl alcohol.

Examples of the inorganic fine particles or the inorganic pigment other than the zinc oxide powder include calcium carbonate, calcium phosphate (apatite), magnesium carbonate, calcium silicate, magnesium silicate, aluminum silicate, kaolin, talc, titanium oxide, aluminum oxide, yellow oxide of iron, γ-iron oxide, cobalt titanate, cobalt violet, silicon oxide and the like.

The sunscreen cosmetic material may further include at least one organic ultraviolet absorber.

Examples of the organic ultraviolet absorber include a benzotriazole-based ultraviolet absorber, a benzoyl methane-based ultraviolet absorber, a benzoic acid-based ultraviolet absorber, an anthranilic acid-based ultraviolet absorber, a salicylic acid-based ultraviolet absorber, a cinnamic acid-based ultraviolet absorber, a silicone-based cinnamic acid ultraviolet absorber, organic ultraviolet absorbers other than the above-described ultraviolet absorbers and the like.

Examples of the benzotriazole-based ultraviolet absorber include 2,2'-hydroxy-5-methylphenylbenzotriazole, 2-(2'-hydroxy-5'-t-octylphenyl)benzotriazole, 2-(2'-hydroxy-5'-methylphenylbenzotriazole and the like.

Examples of the benzoyl methane-based ultraviolet absorber include dibenzalazine, dianisoylmethane, 4-tert-butyl-4'-methoxydibenzoylmethane, 1-(4'-isopropylphenyl)-3-phenyl propane-1,3-dione, 5-(3,3'-dimethyl-2-norbornylidene)-3-pentane-2-one and the like.

Examples of the benzoic acid-based ultraviolet absorber include para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester and the like.

Examples of the anthranilic acid-based ultraviolet absorber include homo methyl-N-acetyl anthranilate and the like.

Examples of the salicylic acid-based ultraviolet absorber include amyl salicylate, methyl salicylate, homo menthyl salicylate, octyl salicylate, phenyl salicylate, benzyl salicylate, p-2-propnol phenyl salicylate and the like.

Examples of the cinnamic acid-based ultraviolet absorber include octyl methoxycinnamate, di-para methoxy cinnamate-mono-2-glyceryl ethylhexanoate, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnmate), 2-ethoxyethyl-p-methoxy cinnamate, cyclohexyl-p-methoxy cinnamate, ethyl-$\alpha$-cyano-$\beta$-phenyl cinnamate, 2-ethylhexyl-$\alpha$-cyano-$\beta$-phenyl cinnamate, glyceryl mono-2-ethylhexanoyl-diparamethoxy cinnamate and the like.

Examples of the silicone-based cinnamic acid ultraviolet absorber include [3-bis(trimethylsiloxy)methylsilyl-1-methylpropyl]-3,4,5-trimethoxy cinnamate, [3-bis(trimethylsiloxy)methylsilyl-3-methylpropyl]-3,4,5-trimethoxy cinnamate, [3-bis(trimethylsiloxy)methylsilylpropyl]-3,4,5-trimethoxy cinnamate, [3-bis(trimethylsiloxy)methylsilylbutyl]-3,4,5-trimethoxy cinnamate, [3-tris(trimethylsiloxy)silylbutyl]-3,4,5-trimethoxy cinnamate, [3-tris(trimethylsiloxy)silyl-1-methylpropyl]-3,4-dimethoxy cinnamate, and the like.

Examples of the organic ultraviolet absorbers other than the above-described ultraviolet absorbers include 3-(4'-methylbenzylidene)-d,l-camphor, 3-benzylidene-d,l-camphor, urocanic acid, ethyl urocanate esters, 2-phenyl-5-methyl benzoxazole, 5-(3,3'-dimethyl-2-norbornylidene)-3-pentane-2-one, silicone-denatured ultraviolet absorbers, fluorine-denatured ultraviolet absorbers and the like.

Among the cosmetic materials of the present embodiment, the critical wavelength of the cosmetic material including the above-described zinc oxide powder of the second embodiment is preferably 370 nm or more. When the critical wavelength of the cosmetic material is 370 nm or more, it is possible to shield ultraviolet rays in a wide range of long-wavelength ultraviolet rays (UVA) and short-wavelength ultraviolet rays (UVB).

As described above, according to the zinc oxide powder of the present embodiment, since the specific surface area, the conductivity and the bulk specific volume are adjusted to the predetermined ranges, it is possible to uniformly disperse the zinc oxide powder even when 50% by mass or more of the zinc oxide powder is dispersed in a dispersion medium. In addition, even when the zinc oxide powder is included at a high concentration in the dispersion medium, the zinc oxide powder is uniformly dispersed and therefore it is possible to obtain an effect of high transparency as in the related art in a case in which the zinc oxide powder is mixed with other components.

In addition, it becomes possible to mix the zinc oxide powder with other components in a state in which the zinc oxide powder is dispersed at a high concentration, and therefore it is possible to improve the degree of freedom in blending through which the other components are provided.

In addition, in a case in which the content of the water-soluble substances in the zinc oxide powder is 0.08% by mass or less, it is possible to obtain a uniform and excellent dispersion having a higher solid content concentration.

In the surface-treated zinc oxide powder of the present embodiment, at least a part of the surface of the zinc oxide powder of the present embodiment is preferably treated with at least one of the inorganic component and the organic component. In this case, it is possible to suppress the surface activity of zinc oxide and to improve the dispersibility of zinc oxide in a dispersion medium. In addition, even in a case in which the zinc oxide powder is included at a high concentration, the zinc oxide powder is uniformly dispersed, and thus it is possible to obtain the effect of high transparency as in the related art in a case in which the zinc oxide powder is mixed with other components.

In addition, since it becomes possible to mix the zinc oxide powder with other components in a state in which the surface-treated zinc oxide powder is dispersed at a high concentration, it is possible to improve the degree of freedom in blending through which the other components are provided.

In addition, in a case in which the content of the water-soluble substances in the surface-treated zinc oxide powder is 0.08% by mass or less, it is possible to obtain a uniform dispersion having a higher solid content concentration.

In the dispersion of the present embodiment, since the dispersion is a uniform dispersion having a high solid content concentration, it is possible to reduce the amount of a dispersion medium added to obtain the desired effect of zinc oxide in a case in which the dispersion is mixed with other components.

In addition, in a case in which the viscosity of the dispersion is in a range of 5 Pa·s to 300 Pa·s, the handling of the dispersion becomes easy.

In the paint of the present embodiment, since a uniform dispersion having a high solid content concentration is used, it is possible to reduce the amount of a dispersion medium added to obtain the desired effect of zinc oxide in a case in which the paint is mixed with other components.

In the cosmetic material of the present embodiment, the degree of freedom in formulation through which the other components are blended increases since it is possible to blend the zinc oxide powder into the cosmetic material at a high concentration. In addition, it becomes easy to blend a number of other components into the cosmetic material, and thus it is possible to obtain a multifunctional cosmetic material.

EXAMPLES

Hereinafter, preferred examples of the present invention will be more specifically described using Examples and Comparative Examples below. However, the present invention is not limited to the following examples.

Example 1

Production of Zinc Oxide-Containing Dispersion

Zinc oxide powder (A1) (with a specific surface area of 35 m$^2$/g, a conductivity of 8 μS/cm, a bulk specific volume of 5.2 mL/g and an average primary particle diameter of 31 nm) was prepared. After that, cyclopentasiloxane (28.5 parts by mass), PEG-9 polydimethylsiloxyethyl dimethicone (6.5 parts by mass), and the zinc oxide powder (A1, 65 parts by mass) were stirred and dispersed for five minutes using a homo mixer at a stirring rotation speed of 4000 rpm, thereby preparing a dispersion (B1) of Example 1.

The obtained dispersion (B1) did not have any precipitates and was a paste-form dispersion having favorable dispersibility. Meanwhile, the average primary particle diameter was a value computed using a specific surface area value (35 m$^2$/g) and Equation (1).

"Production of Surface-Treated Zinc Oxide-Containing Dispersion"

The zinc oxide powder (A1, 95 parts by mass) and methyl hydrogen polysiloxane (5 parts by mass) were mixed for 30 minutes at room temperature (25° C.) using a Henschel mixer at a stirring rotation speed of 1000 rpm.

Next, the components were stirred for three hours with the temperature increased to 150° C. and the stirring rotation speed increased to 2000 rpm, thereby obtaining surface-treated zinc oxide powder (C1) of Example 1.

The zinc oxide powder (C1) (70 parts by mass), cyclopentasiloxane (23 parts by mass), and PEG-9 polydimethylsiloxyethyl dimethicone (7 parts by mass) were stirred and dispersed for five minutes using a homo mixer at a stirring rotation speed of 4000 rpm, thereby preparing a dispersion (D1) in which the surface-treated zinc oxide powder (C1) was dispersed.

The obtained dispersion (D1) did not have any precipitates and was a paste-form dispersion having favorable dispersibility.

"Oil-in-Water-Type Sunscreen Cream"

The dispersion (D1, 24.5 parts by mass), ethylhexyl methoxycinnamate (20.4 parts by mass), 4-t-butyl-4'-methoxydibenzoylmethane (4.1 parts by mass), squalane (20.4 parts by mass), petrolatum (10.2 parts by mass), stearyl alcohol (6.1 parts by mass), stearic acid (6.1 parts by mass), glyceryl monostearate (6.1 parts by mass) and ethyl polyacrylate (2.1 parts by mass) were mixed together at 70° C., thereby producing an oil-phase component.

Purified water (84.2 parts by mass), dipropylene glycol (13.7 parts by mass), disodium edetate (0.1 parts by mass) and triethanolamine (2.0 parts by mass) were mixed together, thereby producing a water-phase component.

The oil-phase component (49 parts by mass) was added to the water-phase component (51 parts by mass), the components were mixed together using a homo mixer and then were cooled, thereby obtaining oil-in-water-type sunscreen cream (E1) of Example 1.

[Evaluation]

"Evaluation of Water-Soluble Substances in Zinc Oxide Powder (A1)"

The zinc oxide powder (A1, 5 g) was weighed, pure water (70 mL) was added to the zinc oxide powder (A1), and the liquid mixture of the zinc oxide powder (A1) and the pure water were boiled for five minutes. Next, the liquid mixture was cooled, then, pure water was added to the liquid mixture to be 100 mL, furthermore, the pure water and the liquid mixture were mixed together, and then the mixture was filtered. Next, the first 10 mL of the filtrate was removed, the subsequently-obtained 40 mL of the filtrate was sampled, the sampled filtrate was evaporated and dried on a water bath, subsequently, was further dried at 105° C. for one hour. Next, the mass of the dry residue was measured, and the percentage of a value obtained by dividing the mass of the dry residue by the initially-weighed mass of the zinc oxide powder (A1) was computed as the content of the water-soluble substances included in the zinc oxide powder (A1). The results are described in Table 1.

"Evaluation of Viscosities of Dispersion (B1) and Dispersion (D1)"

The viscosities of the dispersion (B1) including the zinc oxide powder and the dispersion (D1) including the surface-treated zinc oxide powder (C1) were measured using a digital viscometer (product name: DV-I+Viscometer, manufactured by Brookfield Engineering) under conditions of 25° C. and 20 rpm. The results are described in Table 1.

"Evaluation of Transparency of Oil-in-Water-Type Sunscreen Cream (E1)"

The oil-in-water-type sunscreen cream (E1) was applied onto a silica glass plate so that the application amount reached 2 mg/cm$^2$, thereby forming a coated film on the silica glass plate. The transparency of the coated film at this time was visually evaluated. The evaluation standards are as described below. The results are described in Table 1.

A: The transparency was extremely high
B: The transparency was high
C: The transparency was normal
D: The transparency was low "Evaluation of Ultraviolet-Shielding Properties of Oil-in-Water-Type Sunscreen Cream (E1)"

The oil-in-water-type sunscreen cream (E1) was applied onto a silica glass plate so that the application amount reached 2 mg/cm$^2$ and was naturally dried for 15 minutes, thereby forming a coated film on the silica glass plate. The spectral transmittance of the coated film in the ultraviolet region was measured at six positions using an SPF analyzer UV-1000S (manufactured by Labsphere, Inc.), and the SPF values were computed. The average values of the SPF values at the six positions are described in Table 1.

Example 2

Zinc oxide powder (A2) (with a specific surface area of 35 m$^2$/g, a conductivity of 25 μS/cm a bulk specific volume of 5.3 mL/g, and an average primary particle diameter of 31 nm) was prepared instead of the zinc oxide powder (A1). A dispersion (B2) including the zinc oxide powder (A2), surface-treated zinc oxide powder (C2), a dispersion (D2) including the surface-treated zinc oxide powder (C2) and oil-in-water-type sunscreen cream (E2) of Example 2 were obtained in the same manner as in Example 1 except that the zinc oxide powder (A2) was used.

The obtained dispersion (B2) and dispersion (D2) did not have any precipitates and were paste-form dispersions having favorable dispersibility.

The zinc oxide powder (A2), the dispersion (B2), the dispersion (D2) and the oil-in-water-type sunscreen cream (E2) were evaluated in the same manner as in Example 1. The results are described in Table 1.

Example 3

Zinc oxide powder (A3) (with a specific surface area of 35 m$^2$/g, a conductivity of 80 μS/cm, a bulk specific volume of 5.1 mL/g and an average primary particle diameter of 31 nm) was prepared instead of the zinc oxide powder (A1). A dispersion (B3) including the zinc oxide powder (A3), surface-treated zinc oxide powder (C3), a dispersion (D3) including the surface-treated zinc oxide powder (C3) and oil-in-water-type sunscreen cream (E3) of Example 3 were obtained in the same manner as in Example 1 except that the zinc oxide powder (A3) was used.

The obtained dispersion (B3) and dispersion (D3) did not have any precipitates and were paste-form dispersions having favorable dispersibility.

The zinc oxide powder (A3), the dispersion (B3), the dispersion (D3) and the oil-in-water-type sunscreen cream (E3) were evaluated in the same manner as in Example 1. The results are described in Table 1.

Example 4

Zinc oxide powder (A4) (with a specific surface area of 35 m$^2$/g, a conductivity of 140 μS/cm, a bulk specific volume of 5.2 mL/g and an average primary particle diameter of 31 nm) was prepared instead of the zinc oxide powder (A1). A dispersion (B4) including the zinc oxide powder (A4), surface-treated zinc oxide powder (C4), a dispersion (D4) including the surface-treated zinc oxide powder (C4) and oil-in-water-type sunscreen cream (E4) of Example 4 were obtained in the same manner as in Example 1 except that the zinc oxide powder (A4) was used.

The obtained dispersion (B4) and dispersion (D4) did not have any precipitates and were paste-form dispersions having favorable dispersibility.

The zinc oxide powder (A4), the dispersion (B4), the dispersion (D4) and the oil-in-water-type sunscreen cream (E4) were evaluated in the same manner as in Example 1. The results are described in Table 1.

Example 5

Zinc oxide powder (A5) (with a specific surface area of 10 m$^2$/g, a conductivity of 8 μS/cm, a bulk specific volume of 3.1 mL/g and an average primary particle diameter of 107 nm) was prepared instead of the zinc oxide powder (A1). A dispersion (B5) including the zinc oxide powder (A5), surface-treated zinc oxide powder (C5), a dispersion (D5) including the surface-treated zinc oxide powder (C5) and oil-in-water-type sunscreen cream (E5) of Example 5 were obtained in the same manner as in Example 1 except that the zinc oxide powder (A5) was used.

The obtained dispersion (B5) and dispersion (D5) did not have any precipitates and were paste-form dispersions having favorable dispersibility.

The zinc oxide powder (A5), the dispersion (B5), the dispersion (D5) and the oil-in-water-type sunscreen cream (E5) were evaluated in the same manner as in Example 1. The results are described in Table 1.

Example 6

Zinc oxide powder (A6) (with a specific surface area of 60 m$^2$/g, a conductivity of 8 μS/cm, a bulk specific volume of 5.5 mL/g and an average primary particle diameter of 18 nm) was prepared instead of the zinc oxide powder (A1). A dispersion (B6) including the zinc oxide powder (A6), surface-treated zinc oxide powder (C6), a dispersion (D6) including the surface-treated zinc oxide powder (C6) and oil-in-water-type sunscreen cream (E6) of Example 6 were obtained in the same manner as in Example 1 except that the zinc oxide powder (A6) was used.

The obtained dispersion (B6) and dispersion (D6) did not have any precipitates and were paste-form dispersions having favorable dispersibility.

The zinc oxide powder (A6), the dispersion (B6), the dispersion (D6) and the oil-in-water-type sunscreen cream (E6) were evaluated in the same manner as in Example 1. The results are described in Table 1.

Example 7

Zinc oxide powder (A7) (with a specific surface area of 35 m$^2$/g, a conductivity of 5 μS/cm, a bulk specific volume of 9.5 mL/g and an average primary particle diameter of 31 nm) was prepared instead of the zinc oxide powder (A1). A dispersion (B7) including the zinc oxide powder (A7), surface-treated zinc oxide powder (C7), a dispersion (D7) including the surface-treated zinc oxide powder (C7) and oil-in-water-type sunscreen cream (E7) of Example 7 were obtained in the same manner as in Example 1 except that the zinc oxide powder (A7) was used.

The obtained dispersion (B7) and dispersion (D7) did not have any precipitates and were paste-form dispersions having favorable dispersibility.

The zinc oxide powder (A7), the dispersion (B7), the dispersion (D7), and the oil-in-water-type sunscreen cream (E7) were evaluated in the same manner as in Example 1. The results are described in Table 1.

Example 8

Zinc oxide powder (A8) (with a specific surface area of 35 m$^2$/g, a conductivity of 80 μS/cm, a bulk specific volume of 1.7 mL/g and an average primary particle diameter of 31 nm) was prepared instead of the zinc oxide powder (A1). A dispersion (B8) including the zinc oxide powder (A8), surface-treated zinc oxide powder (C8), a dispersion (D8) including the surface-treated zinc oxide powder (C8) and oil-in-water-type sunscreen cream (E8) of Example 8 were obtained in the same manner as in Example 1 except that the zinc oxide powder (A8) was used.

The obtained dispersion (B8) and dispersion (D8) did not have any precipitates and were paste-form dispersions having favorable dispersibility.

The zinc oxide powder (A8), the dispersion (B8), the dispersion (D8) and the oil-in-water-type sunscreen cream (E8) were evaluated in the same manner as in Example 1. The results are described in Table 1.

Comparative Example 1

Zinc oxide powder (A9) (with a specific surface area of 35 m$^2$/g, a conductivity of 200 μS/cm, a bulk specific volume of 5.2 mL/g, zinc oxide powder was produced with a smaller number of times of washing than that of the zinc oxide powders of the examples, and an average primary particle diameter of 31 nm) was prepared instead of the zinc oxide powder (A1. An attempt was made to produce a dispersion (B9) including the zinc oxide powder (A9) of Comparative Example 1 in the same manner as in Example 1 except that the zinc oxide powder (A9) was used. However, the zinc oxide powder (A9) was separated and thus a uniform dispersion could not be obtained.

Surface-treated zinc oxide powder (C9) of Comparative Example 1 was obtained in the same manner as in Example 1 except that the zinc oxide powder (A9) was used instead of the zinc oxide powder (A1). An attempt was made to produce a dispersion (D9) including the surface-treated zinc oxide powder (C9) in the same manner as in Example 1 except that the surface-treated zinc oxide powder (C9) was used instead of the surface-treated zinc oxide powder (C1). However, the surface-treated zinc oxide powder (C9) was separated and thus a uniform dispersion (D9) could not be obtained.

Therefore, it was not possible to produce a sunscreen cream (E9).

The zinc oxide powder (A9) was evaluated in the same manner as in Example 1. The results are described in Table 1.

Reference Example 1

Cyclopentasiloxane (55.5 parts by mass), PEG-9 polydimethylsiloxyethyl dimethicone (4.0 parts by mass), and the zinc oxide powder (A9, 40 parts by mass) were stirred and dispersed for five minutes using a homo mixer at a stirring rotation speed of 4000 rpm, thereby preparing a dispersion having a low solid content concentration.

The obtained dispersion having a low solid content concentration did not have any precipitates and was a dispersion having favorable dispersibility.

Comparative Example 2

Zinc oxide powder (A10) (with a specific surface area of 35 $m^2/g$, a conductivity of 5 μS/cm, a bulk specific volume of 12.1 mL/g, a raw material having a higher bulk specific volume than the raw material used in the example was used, and an average primary particle diameter of 31 nm) was prepared instead of the zinc oxide powder (A1). An attempt was made to produce a dispersion (B10) including the zinc oxide powder (A10) of Comparative Example 2 in the same manner as in Example 1 except that the zinc oxide powder (A10) was used. However, the zinc oxide powder (A10) was separated and thus a uniform dispersion could not be obtained.

Surface-treated zinc oxide powder (C10) of Comparative Example 2 was obtained in the same manner as in Example 1 except that the zinc oxide powder (A10) was used instead of the zinc oxide powder (A1). An attempt was made to produce a dispersion (D10) including the surface-treated zinc oxide powder (C10) in the same manner as in Example 1 except that the surface-treated zinc oxide powder (C10) was used instead of the surface-treated zinc oxide powder (C1). However, the surface-treated zinc oxide powder (C10) was separated and thus a uniform dispersion (D10) could not be obtained.

Therefore, it was not possible to produce a sunscreen cream (E10).

The zinc oxide powder (A10) was evaluated in the same manner as in Example 1. The results are described in Table 1.

Reference Example 2

Cyclopentasiloxane (55.5 parts by mass), PEG-9 polydimethylsiloxyethyl dimethicone (4.0 parts by mass) and the zinc oxide powder (A10, 40 parts by mass) were stirred and dispersed for five minutes using a homo mixer at a stirring rotation speed of 4000 rpm, thereby preparing a dispersion having a low solid content concentration.

The obtained dispersion having a low solid content concentration did not have any precipitates and was a dispersion having favorable dispersibility.

Comparative Example 3

Comparative Reference Example

Zinc oxide powder (A11) (with a specific surface area of 5 $m^2/g$, a conductivity of 8 μS/cm, a bulk specific volume of 2.1 mL/g, zinc oxide powder having a greater average primary particle diameter than that of the zinc oxide powders of the examples, and an average primary particle diameter of 214 nm) was prepared instead of the zinc oxide powder (A1). A dispersion (B11) including the zinc oxide powder (A11), surface-treated zinc oxide powder (C11), a dispersion (D11) including the surface-treated zinc oxide powder (C11) and oil-in-water-type sunscreen cream (E11) of Comparative Example 3 were obtained in the same manner as in Example 1 except that the zinc oxide powder (A11) was used.

The obtained dispersion (B11) and dispersion (D11) did not have any precipitates and were paste-form dispersions having favorable dispersibility.

The zinc oxide powder (A11), the dispersion (B11), the dispersion (D11) and the oil-in-water-type sunscreen cream (E11) were evaluated in the same manner as in Example 1. The results are described in Table 1.

TABLE 1

|  | Example 1 | Example 2 | Example 3 | Example 4 | Example 5 | Example 6 | Example 7 | Example 8 | Comparative Example 1 | Comparative Example 2 | Comparative Example 3 |
|---|---|---|---|---|---|---|---|---|---|---|---|
| Specific surface area of A [$m^2/g$] | 35 | 35 | 35 | 35 | 10 | 60 | 35 | 35 | 35 | 35 | 5 |
| Conductivity of A [μS/cm] | 8 | 25 | 80 | 140 | 8 | 8 | 5 | 80 | 200 | 5 | 8 |
| Bulk specific volume of A [mL/g] | 5.2 | 5.3 | 5.1 | 5.2 | 3.1 | 5.5 | 9.5 | 1.7 | 5.2 | 12.1 | 2.1 |
| Content of water-soluble substances in A [% by mass] | <0.05 | <0.05 | 0.05 | 0.05 | <0.05 | <0.05 | <0.05 | 0.08 | 0.1 | <0.05 | <0.05 |
| Viscosity of B [Pa · s] | 25 | 25 | 27 | 27 | 24 | 25 | 31 | 23 | — | — | 20 |
| Viscosity of D [Pa · s] | 30 | 30 | 32 | 32 | 29 | 30 | 35 | 28 | — | — | 25 |

TABLE 1-continued

|  | Example 1 | Example 2 | Example 3 | Example 4 | Example 5 | Example 6 | Example 7 | Example 8 | Comparative Example 1 | Comparative Example 2 | Comparative Example 3 |
|---|---|---|---|---|---|---|---|---|---|---|---|
| Transparency of E | A | A | A | A | B | A | A | A | — | — | D |
| SPF value of E | 55 | 55 | 55 | 55 | 45 | 55 | 55 | 55 | — | — | 40 |

From the results in Table 1, it was confirmed that, when zinc oxide powder was used which has a specific surface area, a conductivity and a bulk specific volume within the predetermined ranges as in Examples 1 to 8, a uniform dispersion having high transparency and a high solid content concentration can be obtained.

Example 9

Evaluation of Zinc Oxide Powder

The following evaluations were carried out using zinc oxide powder (A12) (with a specific surface area of 5.0 m$^2$/g, a conductivity of 5 μS/cm, a bulk specific volume of 2.0 mL/g, less than 0.05% by mass of the water-soluble substances, and an average primary particle diameter of 214 nm).

(Mixing Test of Oleic Acid)

Oleic acid (20 parts by mass) and isopropyl alcohol (80 parts by mass) were mixed together, thereby preparing a 20% by mass oleic acid isopropyl alcohol solution. The zinc oxide powder (A12, 10 parts by mass) was added to this 20% by mass oleic acid isopropyl alcohol solution (50 parts by mass), and the components were stirred and then left to stand for 48 hours. In this way, an isopropyl alcohol suspension containing zinc oxide and oleic acid was generated.

The fluidity of the suspension was visually observed after 48 hours from the completion of the preparation, and the observation results were evaluated into the following three steps.

A: Low-viscosity liquid phase
B: Gel phase
C: Solidified

The results are described in Table 2.

(Primary Particle Diameter of Zinc Oxide Powder)

The zinc oxide powder was photographed using a scanning electron microscope (SEM).

Next, 150 primary particles of zinc oxide were selected, and the longest diameter of multiple diameters passing through the center points of these fine particles was selected and used as the primary particle diameter.

The results are described in Table 2.

"Production of Zinc Oxide-Containing Dispersion"

Cyclopentasiloxane (28.5 parts by mass), PEG-9 polydimethylsiloxyethyl dimethicone (6.5 parts by mass), and the zinc oxide powder (A12, 75 parts by mass) were stirred and dispersed for ten minutes using a homo mixer at a stirring rotation speed of 5000 rpm, thereby preparing a dispersion (B12) of Example 9.

The obtained dispersion (B12) did not have any precipitates and was a paste-form dispersion having favorable dispersibility.

"Production of Surface-Treated Zinc Oxide-Containing Dispersion"

The zinc oxide powder (A12, 98 parts by mass) and methyl hydrogen polysiloxane (2 parts by mass) were mixed at room temperature (25° C.) for 30 minutes using a Henschel mixer at a stirring rotation speed of 1000 rpm.

Next, the components were stirred for three hours with the temperature increased to 150° C. and the stirring rotation speed increased to 2000 rpm, thereby obtaining surface-treated zinc oxide powder (C12) of Example 9.

The zinc oxide powder (C12) (78 parts by mass), cyclopentasiloxane (14.2 parts by mass) and PEG-9 polydimethylsiloxyethyl dimethicone (7.8 parts by mass) were stirred and dispersed for ten minutes using a homo mixer at a stirring rotation speed of 5000 rpm, thereby preparing a dispersion (D12) in which the surface-treated zinc oxide powder (C12) was dispersed.

The obtained dispersion (D12) did not have any precipitates and was a paste-form dispersion having favorable dispersibility.

"Oil-in-Water-Type Sunscreen Cream"

The dispersion (D12, 21.3 parts by mass), ethylhexyl methoxycinnamate (20.4 parts by mass), 4-t-butyl-4'-methoxydibenzoylmethane (4.1 parts by mass), squalane (20.4 parts by mass), petrolatum (10.2 parts by mass), stearyl alcohol (6.1 parts by mass), stearic acid (6.1 parts by mass), glyceryl monostearate (6.1 parts by mass), and ethyl polyacrylate (2.1 parts by mass) were mixed together at 70° C., thereby producing an oil-phase component.

Purified water (87.2 parts by mass), dipropylene glycol (13.7 parts by mass), disodium edetate (0.1 parts by mass) and triethanolamine (2.0 parts by mass) were mixed together, thereby producing a water-phase component.

The oil-phase component (49 parts by mass) was added to the water-phase component (51 parts by mass), the components were mixed together using a homo mixer and then were cooled, thereby obtaining oil-in-water-type sunscreen cream (E12) of Example 9.

[Evaluation]

"Evaluation of Viscosities of Dispersion (B12) and Dispersion (D12)"

The viscosities of the dispersion (B12) including the zinc oxide powder (A12) and the dispersion (D12) including the surface-treated zinc oxide powder (C12) were measured using a digital viscometer (product name: DV-I+Viscometer, manufactured by Brookfield Engineering) under conditions of 25° C. and 20 rpm. The results are described in Table 3.

"Evaluation of Critical Wavelength of Dispersion (B12)"

The dispersion (B12) was diluted with cyclopentasiloxane so that the concentration of zinc oxide reached 5% by mass.

Next, the diluted dispersion (B12) was applied onto a silica glass plate so that the thickness reached 12 μm and was naturally dried for 15 minutes, thereby forming a coated film on the silica glass plate.

The spectral transmittance of the coated film in the ultraviolet region was measured at six positions using an SPF analyzer UV-1000S (manufactured by Labsphere, Inc.) and the critical wavelengths of the dispersion (B12) were computed. The average values of the critical wavelengths at the six positions are described in Table 3.

"Evaluation of Ultraviolet-Shielding Properties of Oil-in-Water-Type Sunscreen Cream (E12)"

The oil-in-water-type sunscreen cream (E12) was applied onto a silica glass plate so that the application amount reached 2 mg/cm² and was naturally dried for 15 minutes, thereby forming a coated film on the silica glass plate. The spectral transmittance of the coated film in the ultraviolet region was measured at six positions using an SPF analyzer UV-1000S (manufactured by Labsphere, Inc.) and the SPF values and the critical wavelengths were computed. The average values of the SPF values and the critical wavelengths at the six positions are described in Table 3.

"Evaluation of Transparency of Oil-in-Water-Type Sunscreen Cream (E12)"

The oil-in-water-type sunscreen cream (E12) was applied onto a silica glass plate so that the application amount reached 2 mg/cm² and was naturally dried for 15 minutes, thereby forming a coated film on the silica glass plate. The transparency of the coated film was visually evaluated. The evaluation standards are as described below. The results are described in Table 3.

A: The transparency was extremely high
B: The transparency was high
C: The transparency was normal
D: The transparency was low Example 10

A dispersion (B13) including zinc oxide powder (A13), surface-treated zinc oxide powder (C13), a dispersion (D13) including the surface-treated zinc oxide powder (C13) and oil-in-water-type sunscreen cream (E13) of Example 10 were obtained in the same manner as in Example 9, except that the zinc oxide powder (A13) (with a specific surface area of 5.0 m²/g, a conductivity of 25 μS/cm, a bulk specific volume of 1.9 mL/g, less than 0.05% by mass of the water-soluble substances, and an average primary particle diameter of 214 nm) was used instead of the zinc oxide powder (A12).

The obtained dispersion (B13) and dispersion (D13) did not have any precipitates and were paste-form dispersions having favorable dispersibility.

The zinc oxide powder (A13), the dispersion (B13), the dispersion (D13) and the oil-in-water-type sunscreen cream (E13) were evaluated in the same manner as in Example 9.

The evaluation results of Example 10 are described in Tables 2 and 3.

Example 11

A dispersion (B14) including zinc oxide powder (A14), surface-treated zinc oxide powder (C14), a dispersion (D14) including the surface-treated zinc oxide powder (C14) and oil-in-water-type sunscreen cream (E14) of Example 11 were obtained in the same manner as in Example 9, except that zinc oxide powder (A14) (with a specific surface area of 5.0 m²/g, a conductivity of 80 μS/cm, a bulk specific volume of 2.0 mL/g, less than 0.05% by mass of the water-soluble substances, and an average primary particle diameter of 214 nm) was used instead of the zinc oxide powder (A12).

The obtained dispersion (B14) and dispersion (D14) did not have any precipitates and were paste-form dispersions having favorable dispersibility.

The zinc oxide powder (A14), the dispersion (B14), the dispersion (D14) and the oil-in-water-type sunscreen cream (E14) were evaluated in the same manner as in Example 9.

The evaluation results of Example 11 are described in Tables 2 and 3.

Example 12

A dispersion (B15) including zinc oxide powder (A15), surface-treated zinc oxide powder (C15), a dispersion (D15) including the surface-treated zinc oxide powder (C15) and oil-in-water-type sunscreen cream (E15) of Example 12 were obtained in the same manner as in Example 9, except that zinc oxide powder (A15) (with a specific surface area of 5.0 m²/g, a conductivity of 140 μS/cm, a bulk specific volume of 2.1 mL/g, less than 0.08% by mass of the water-soluble substances, and an average primary particle diameter of 214 nm) was used instead of the zinc oxide powder (A12).

The obtained dispersion (B15) and dispersion (D15) did not have any precipitates and were paste-form dispersions having favorable dispersibility.

The zinc oxide powder (A15), the dispersion (B15), the dispersion (D15) and the oil-in-water-type sunscreen cream (E15) were evaluated in the same manner as in Example 9.

The evaluation results of Example 12 are described in Tables 2 and 3.

Example 13

A dispersion (B16) including zinc oxide powder (A16), surface-treated zinc oxide powder (C16), a dispersion (D16) including the surface-treated zinc oxide powder (C16) and oil-in-water-type sunscreen cream (E16) of Example 13 were obtained in the same manner as in Example, except that zinc oxide powder (A16) (with a specific surface area of 2.0 m²/g, a conductivity of 5 μS/cm, a bulk specific volume of 1.1 mL/g, less than 0.05% by mass of the water-soluble substances, and an average primary particle diameter of 535 nm) was used instead of the zinc oxide powder (A12).

The obtained dispersion (B16) and dispersion (D16) did not have any precipitates and were paste-form dispersions having favorable dispersibility.

The zinc oxide powder (A16), the dispersion (B16), the dispersion (D16) and the oil-in-water-type sunscreen cream (E16) were evaluated in the same manner as in Example 9.

The evaluation results of Example 13 are described in Tables 2 and 3.

Example 14

A dispersion (B17) including zinc oxide powder (A17), surface-treated zinc oxide powder (C17), a dispersion (D17) including the surface-treated zinc oxide powder (C17) and oil-in-water-type sunscreen cream (E17) of Example 14 were obtained in the same manner as in Example 9, except that zinc oxide powder (A17) (with a specific surface area of 7.9 m²/g, a conductivity of 5 μS/cm, a bulk specific volume of 4.2 mL/g, less than 0.05% by mass of the water-soluble substances, and an average primary particle diameter of 135 nm) was used instead of the zinc oxide powder (A12).

The obtained dispersion (B17) and dispersion (D17) did not have any precipitates and were paste-form dispersions having favorable dispersibility.

The zinc oxide powder (A17), the dispersion (B17), the dispersion (D17) and the oil-in-water-type sunscreen cream (E17) were evaluated in the same manner as in Example 9.

The evaluation results of Example 14 are described in Tables 2 and 3.

Example 15

A dispersion (B18) including zinc oxide powder (A18), surface-treated zinc oxide powder (C18), a dispersion (D18)

including the surface-treated zinc oxide powder (C18) and oil-in-water-type sunscreen cream (E18) of Example 15 were obtained in the same manner as in Example 9, except that zinc oxide powder (A18) (with a specific surface area of 2.0 m²/g, a conductivity of 5 µS/cm, a bulk specific volume of 0.5 mL/g, less than 0.05% by mass of the water-soluble substances, and an average primary particle diameter of 535 nm) was used instead of the zinc oxide powder (A12).

The obtained dispersion (B18) and dispersion (D18) did not have any precipitates and were paste-form dispersions having favorable dispersibility.

The zinc oxide powder (A18), the dispersion (B18), the dispersion (D18) and the oil-in-water-type sunscreen cream (E18) were evaluated in the same manner as in Example 9.

The evaluation results of Example 15 are described in Tables 2 and 3.

Example 16

A dispersion (B19) including zinc oxide powder (A19), surface-treated zinc oxide powder (C19), a dispersion (D19) including the surface-treated zinc oxide powder (C19) and oil-in-water-type sunscreen cream (E19) of Example 16 were obtained in the same manner as in Example, except that zinc oxide powder (A19) (with a specific surface area of 7.9 m²/g, a conductivity of 5 µS/cm, a bulk specific volume of 6.0 mL/g, less than 0.05% by mass of the water-soluble substances, and an average primary particle diameter of 135 nm) was used instead of the zinc oxide powder (A12).

The obtained dispersion (B19) and dispersion (D19) did not have any precipitates and were paste-form dispersions having favorable dispersibility.

The zinc oxide powder (A19), the dispersion (B19), the dispersion (D19) and the oil-in-water-type sunscreen cream (E19) were evaluated in the same manner as in Example 9.

The evaluation results of Example 16 are described in Tables 2 and 3.

Comparative Example 4

An attempt was made to produce a dispersion (B20) including zinc oxide powder (A20) of Comparative Example 4 in the same manner as in Example 9 except that zinc oxide powder (A20) (with a specific surface area of 5.0 m²/g, a conductivity of 200 µS/cm, a bulk specific volume of 2.0 mL/g, less than 0.10% by mass of the water-soluble substances, and an average primary particle diameter of 214 nm) was used instead of the zinc oxide powder (A12). However, the zinc oxide powder (A20) was separated and thus a uniform dispersion could not be obtained.

Surface-treated zinc oxide powder (C20) of Comparative Example 4 was obtained in the same manner as in Example 9, except that the zinc oxide powder (A20) was used instead of the zinc oxide powder (A12). An attempt was made to produce a dispersion (D20) including the surface-treated zinc oxide powder (C20) in the same manner as in Example 9 except that the surface-treated zinc oxide powder (C20) was used instead of the surface-treated zinc oxide powder (C12). However, the surface-treated zinc oxide powder (C20) was separated and thus a uniform dispersion (D20) could not be obtained.

Therefore, it was not possible to produce a sunscreen cream (E20).

The zinc oxide powder (A20) was evaluated in the same manner as in Example 9.

The evaluation results of Comparative Example 4 are described in Tables 4 and 5.

Reference Example 3

Cyclopentasiloxane (55.5 parts by mass), PEG-9 polydimethylsiloxyethyl dimethicone (4.0 parts by mass) and the zinc oxide powder (A20, 40 parts by mass) were stirred and dispersed for ten minutes using a homo mixer at a stirring rotation speed of 5000 rpm, thereby preparing a dispersion (B20-2) having a low solid content concentration.

The obtained dispersion (B20-2) having a low solid content concentration did not have any precipitates and was a dispersion having favorable dispersibility.

The critical wavelength was measured using the dispersion (B20-2) in the same manner as in Example 9.

The evaluation results of Reference Example 3 are described in Tables 4 and 5.

Comparative Example 5

A dispersion (B21) including zinc oxide powder (A21), surface-treated zinc oxide powder (C21), a dispersion (D21) including the surface-treated zinc oxide powder (C21) and oil-in-water-type sunscreen cream (E21) of Comparative Example 5 were obtained in the same manner as in Example 9, except that the zinc oxide powder (A21) (with a specific surface area of 1.0 m²/g, a conductivity of 5 µS/cm, a bulk specific volume of 0.7 mL/g, less than 0.05% by mass of the water-soluble substances, an average primary particle diameter of 1070 nm, and zinc oxide powder having a greater average primary particle diameter than the zinc oxide powders of the examples) was used instead of the zinc oxide powder (A12).

The obtained dispersion (B21) and dispersion (D21) did not have any precipitates and were paste-form dispersions having favorable dispersibility.

The zinc oxide powder (A21), the dispersion (B21), the dispersion (D21) and the oil-in-water-type sunscreen cream (E21) were evaluated in the same manner as in Example 9.

The oil-in-water-type sunscreen cream (E21) had a lower SPF than the sunscreen creams of the examples, also had poor transparency when applied to the skin, and had a whitish appearance.

The evaluation results of Comparative Example 5 are shown in Tables 4 and 5.

Comparative Example 6

Zinc oxide powder (A22) was added to the oleic acid isopropyl alcohol solution in the same manner as in Example 9, except that the zinc oxide powder (A22) (with a specific surface area of 15.0 m²/g, a conductivity of 5 µS/cm, a bulk specific volume of 4.5 mL/g, less than 0.05% by mass of the water-soluble substances, an average primary particle diameter of 71 nm, and zinc oxide powder having a smaller average primary particle diameter than the zinc oxide powders of the examples) was used instead of the zinc oxide powder (A12). As a result, it was not possible to mix the zinc oxide powder (A22) in. Therefore, other evaluations were not carried out for the zinc oxide powder (A22).

The evaluation results of Comparative Example 6 are described in Tables 4 and 5.

Reference Example 4

Cyclopentasiloxane (55.5 parts by mass), PEG-9 polydimethylsiloxyethyl dimethicone (4.0 parts by mass) and the zinc oxide powder (A22, 40 parts by mass) were stirred and dispersed for ten minutes using a homo mixer at a stirring rotation speed of 5000 rpm, thereby preparing a dispersion (B22-2) having a low solid content concentration.

The obtained dispersion (B22-2) having a low solid content concentration did not have any precipitates and was a dispersion having favorable dispersibility.

The critical wavelength was measured using the dispersion (B22-2) in the same manner as in Example 9.

The evaluation results of Reference Example 4 are described in Tables 4 and 5.

Comparative Example 7

An attempt was made to produce a dispersion (B23) including zinc oxide powder (A23) of Comparative Example 7 in the same manner as in Example 9, except that zinc oxide powder (A23) (with a specific surface area of 7.9 m$^2$/g, a conductivity of 5 μS/cm, a bulk specific volume of 8.0 mL/g, less than 0.05% by mass of the water-soluble substances, an average primary particle diameter of 135 nm, and zinc oxide powder having a greater bulk specific volume than the zinc oxide powders of the examples) was used instead of the zinc oxide powder (A12). However, the viscosity of the dispersion became higher than in Example 9 and thus the stirring became insufficient, the zinc oxide powder (A23) was separated, and a uniform dispersion could not be obtained.

Surface-treated zinc oxide powder (C23) of Comparative Example 7 was obtained in the same manner as in Example 9, except that the zinc oxide powder (A23) was used instead of the zinc oxide powder (A12). An attempt was made to produce a dispersion (D23) including the surface-treated zinc oxide powder (C23) in the same manner as in Example 9, except that the surface-treated zinc oxide powder (C23) was used instead of the surface-treated zinc oxide powder (C12). However, the viscosity of the dispersion became higher than in Example 9 and thus the stirring became insufficient, the surface-treated zinc oxide powder (C23) was separated, and a uniform dispersion could not be obtained.

Therefore, it was not possible to produce a sunscreen cream (E23).

The zinc oxide powder (A23) was evaluated in the same manner as in Example 9.

The evaluation results of Comparative Example 7 are described in Tables 4 and 5.

Reference Example 5

Cyclopentasiloxane (55.5 parts by mass), PEG-9 polydimethylsiloxyethyl dimethicone (4.0 parts by mass) and the zinc oxide powder (A23, 40 parts by mass) were stirred and dispersed for ten minutes using a homo mixer at a stirring rotation speed of 5000 rpm, thereby preparing a dispersion (B23-2) having a low solid content concentration.

The obtained dispersion (B23-2) having a low solid content concentration did not have any precipitates and was a dispersion having favorable dispersibility.

The critical wavelength was measured using the dispersion (B23-2) in the same manner as in Example 1.

The evaluation results of Reference Example 5 are described in Tables 4 and 5.

TABLE 2

|  | Example 9 | Example 10 | Example 11 | Example 12 | Example 13 | Example 14 | Example 15 | Example 16 |
|---|---|---|---|---|---|---|---|---|
| Specific surface area of A [m$^2$/g] | 5.0 | 5.0 | 5.0 | 5.0 | 2.0 | 7.9 | 2.0 | 7.9 |
| Conductivity of A [μS/cm] | 5 | 25 | 80 | 140 | 5 | 5 | 5 | 5 |
| Bulk specific volume of A [mL/g] | 2.0 | 1.9 | 2.0 | 2.1 | 1.1 | 4.2 | 0.5 | 6.0 |
| Content of water-soluble substances in A [% by mass] | <0.05 | <0.05 | 0.05 | 0.08 | <0.05 | <0.05 | <0.05 | <0.05 |
| Maximum value of primary particle diameter of A [nm] | 400 | 400 | 400 | 400 | 800 | 340 | 570 | 340 |
| Mixing test of oleic acid | A | A | A | A | A | A | A | A |

TABLE 3

|  | Example 9 | Example 10 | Example 11 | Example 12 | Example 13 | Example 14 | Example 15 | Example 16 |
|---|---|---|---|---|---|---|---|---|
| Viscosity of B [Pa·s] | 30 | 30 | 32 | 32 | 28 | 30 | 26 | 35 |
| Critical wavelength of B [nm] | 385 | 385 | 385 | 385 | 387 | 380 | 387 | 381 |
| Viscosity of D [Pa·s] | 35 | 35 | 38 | 38 | 32 | 36 | 30 | 42 |
| Transparency of E | B | B | B | B | C | B | C | B |
| SPF value of E | 50 | 50 | 50 | 50 | 40 | 50 | 40 | 50 |
| Critical wavelength of E [nm] | 380 | 380 | 380 | 380 | 382 | 375 | 381 | 375 |

TABLE 4

|  | Comparative Example 4 | Comparative Example 5 | Comparative Example 6 | Comparative Example 7 | Reference Example 3 | Reference Example 4 | Reference Example 5 |
|---|---|---|---|---|---|---|---|
| Specific surface area of A [m$^2$/g] | 5.0 | 1.0 | 15.0 | 7.9 | 5.0 | 15.0 | 7.9 |
| Conductivity of A [μS/cm] | 200 | 5 | 5 | 5 | 200 | 5 | 5 |
| Bulk specific volume of A [mL/g] | 2.0 | 0.7 | 4.5 | 8.0 | 2.0 | 4.5 | 8.0 |
| Content of water-soluble substances in A [% by mass] | 0.10 | <0.05 | <0.05 | <0.05 | 0.10 | <0.05 | <0.05 |

TABLE 4-continued

|  | Comparative Example 4 | Comparative Example 5 | Comparative Example 6 | Comparative Example 7 | Reference Example 3 | Reference Example 4 | Reference Example 5 |
|---|---|---|---|---|---|---|---|
| Maximum value of primary particle diameter of A [nm] | 400 | 1200 | 250 | 400 | 400 | 250 | 400 |
| Mixing test of oleic acid | A | A | C | A | A | C | A |

TABLE 5

|  | Comparative Example 4 | Comparative Example 5 | Comparative Example 6 | Comparative Example 7 | Reference Example 3 | Reference Example 4 | Reference Example 5 |
|---|---|---|---|---|---|---|---|
| Viscosity of B [Pa · s] | Not dispersable | — | — | Not dispersable | — | — | — |
| Critical wavelength of B [nm] | — | 388 | — | — | 385 | 373 | 380 |
| Viscosity of D [Pa · s] | — | — | — | Not dispersable | — | — | — |
| Transparency of E | — | D | — | — | — | — | — |
| SPF value of E | — | 35 | — | — | — | — | — |
| Critical wavelength of E [nm] | — | 384 | — | — | — | — | — |

From the results of Tables 2 and 3, it was confirmed that, when zinc oxide powder having a specific surface area, a conductivity and a bulk specific volume which were within the predetermined ranges was used as in Examples 9 to 16, a uniform dispersion having high transparency and a high solid content concentration could be obtained and, furthermore, sunscreen cream including the dispersion was excellent in terms of ultraviolet-shielding properties.

On the other hand, it was confirmed from the results of Tables 4 and 5 that, when zinc oxide powder having a specific surface area, a conductivity and a bulk specific volume which were outside the predetermined ranges was used as in Comparative Examples 4 to 7, a uniform dispersion could not be obtained.

INDUSTRIAL APPLICABILITY

The present invention provides zinc oxide powder that can be dispersed in a dispersion medium in a state of a high solid content concentration and a dispersion, paint and a cosmetic material which include the zinc oxide powder.

When dispersed in a dispersion medium so as to produce a dispersion, the zinc oxide powder of the present invention has high transparency and a high solid content concentration and is uniformly dispersed. Therefore, the zinc oxide powder of the present invention is capable of increasing the degree of freedom in blending design in a case in which the zinc oxide powder is applied to a dispersion, paint and an aqueous cosmetic material, and has a great industrial value.

The invention claimed is:

1. Zinc oxide powder, wherein a specific surface area of the powder is in a range of 1.5 m$^2$/g to 65 m$^2$/g, a conductivity of the powder is 150 µS/cm or less and a bulk specific volume of the powder is in a range of 0.5 mL/g to 10 mL/g.

2. The zinc oxide powder according to claim 1, wherein the content of water-soluble substances thereof is 0.08% by mass or less.

3. The zinc oxide powder according to claim 1, wherein the specific surface area of the powder is in a range of 8.0 m$^2$/g to 65 m$^2$/g and the bulk specific volume is in a range of 1 mL/g to 10 mL/g.

4. The zinc oxide powder according to claim 3, wherein the zinc oxide powder has an average particle diameter in a range of 15 nm to 75 nm, wherein the average particle diameter is obtained by the general formula (1);

$$\text{average particle diameter} = 6000/(BET \text{ specific surface area of the powder} \times \rho) \quad (1)$$

($\rho$ represents the density of zinc oxide particles and is set to 5.606 g/cm$^3$ for conversion).

5. The zinc oxide powder according to claim 3, wherein the specific surface area of the powder is in a range of 15.0 m$^2$/g to 60 m$^2$/g and the bulk specific volume is in a range of 1.5 mL/g to 9.5 mL/g.

6. The zinc oxide powder according to claim 3, wherein the specific surface area of the powder is in a range of 20.0 m$^2$/g to 50 m$^2$/g and the bulk specific volume is in a range of 3 mL/g to 8 mL/g.

7. The zinc oxide powder according to claim 3, wherein the specific surface area of the powder is in a range of 25.0 m$^2$/g to 45 m$^2$/g and the bulk specific volume is in a range of 4 mL/g to 7 mL/g.

8. The zinc oxide powder according to claim 1, wherein the specific surface area of the powder is in a range of 1.5 m$^2$/g or more and less than 8.0 m$^2$/g and the bulk specific volume of the powder is in a range of 0.5 mL/g to 6 mL/g.

9. The zinc oxide powder according to claim 8, wherein a maximum value of a primary particle diameter of the particle is 900 nm or less.

10. The zinc oxide powder according to claim 8, wherein the zinc oxide powder has an average particle diameter in a range of 135 nm to 715 nm, wherein the average particle diameter is obtained by the general formula (1);

$$\text{average particle diameter} = 6000/(BET \text{ specific surface area of the powder} \times \rho) \quad (1)$$

($\rho$ represents the density of zinc oxide particles and is set to 5.606 g/cm$^3$ for conversion).

11. The zinc oxide powder according to claim 8, wherein the maximum value of the primary particle diameter of the particle is 800 nm or less.

12. The zinc oxide powder according to claim 8, wherein the maximum value of the primary particle diameter of the particle is 600 nm or less.

13. The zinc oxide powder according to claim 8, wherein the specific surface area of the powder is in a range of 2.0 $m^2/g$ to 7.5 $m^2/g$ and the bulk specific volume of the powder is in a range of 1 mL/g to 5 mL/g.

14. The zinc oxide powder according to claim 8, wherein the specific surface area of the powder is in a range of 3.0 $m^2/g$ to 7.0 $m^2/g$ and the bulk specific volume of the powder is in a range of 2 mL/g to 4 mL/g.

15. The zinc oxide powder according to claim 1, wherein the surfaces thereof are treated with at least one of an inorganic component and an organic component.

16. The zinc oxide powder according to claim 1, wherein the content of water-soluble substances thereof is 0.08% by mass or less, a maximum value of a primary particle diameter of the particle is 900 nm or less, and the surfaces thereof are treated with at least one of an inorganic component and an organic component.

17. A dispersion comprising:
the zinc oxide powder according to claim 1; and
a dispersion medium,
wherein the content of the zinc oxide powder is in a range of 50% by mass to 90% by mass.

18. Paint comprising:
the zinc oxide powder according to claim 1;
a resin; and
a dispersion medium,
wherein a content of the zinc oxide powder is in a range of 10% by mass to 40% by mass.

19. A cosmetic material comprising:
the zinc oxide powder according to claim 1 and a cosmetic base material.

20. The cosmetic material according to claim 19, wherein the cosmetic material comprises a dispersion wherein the zinc oxide powder has been mixed with a dispersion medium to form a dispersion, wherein the dispersion is blended into the cosmetic base material and the content of the zinc oxide powder in the dispersion is in a range of 50% by mass to 90% by mass.

* * * * *